(12) United States Patent
Lunner et al.

(10) Patent No.: US 11,297,444 B2
(45) Date of Patent: Apr. 5, 2022

(54) HEARING AID SYSTEM

(71) Applicant: Oticon A/S, Smørum (DK)

(72) Inventors: Thomas Lunner, Smørum (DK);
Tanveer Bhuiyan, Smørum (DK);
Ariane Laplante-Lévesque, Smørum (DK); José Antonio Esparza Isasa, Smørum (DK); Sergi Rotger Griful, Smørum (DK)

(73) Assignee: Oticon A/S, Smørum (DK)

( * ) Notice: Subject to any disclaimer, the term of this patent is extended or adjusted under 35 U.S.C. 154(b) by 641 days.

(21) Appl. No.: 16/205,934

(22) Filed: Nov. 30, 2018

(65) Prior Publication Data
US 2019/0174238 A1 Jun. 6, 2019

(30) Foreign Application Priority Data
Dec. 1, 2017 (EP) .................................. 17204855

(51) Int. Cl.
*H04R 25/00* (2006.01)
*A61B 5/30* (2021.01)
(Continued)

(52) U.S. Cl.
CPC ......... *H04R 25/505* (2013.01); *A61B 5/0205* (2013.01); *A61B 5/30* (2021.01);
(Continued)

(58) Field of Classification Search
CPC ................................ A61B 5/30; H04R 25/505
(Continued)

(56) References Cited

U.S. PATENT DOCUMENTS

| 2012/0203077 A1 | 8/2012 | He et al. |
| 2016/0094899 A1 | 3/2016 | Aumer et al. |

(Continued)

FOREIGN PATENT DOCUMENTS

| EP | 2 736 273 A1 | 5/2014 |
| EP | 3 035 710 A2 | 6/2016 |
| EP | 3 035 710 A3 | 6/2016 |

*Primary Examiner* — Nadia A Mahmood
(74) *Attorney, Agent, or Firm* — Birch, Stewart, Kolasch & Birch, LLP

(57) ABSTRACT

The invention concerns a hearing aid system that comprises an ear canal member comprising a sensor arrangement. The sensor arrangement comprises at least one surface electrode located at a surface of said ear canal member to allow said at least one surface electrode to contact the skin of a user when said ear canal member is operationally mounted on the user. The at least one surface electrode (150) is adapted to pick up a low voltage electric signal from the user's skin. The sensor arrangement further comprises a light sensor (180) located at a surface of said housing to allow emitting light through skin proximate to the light sensor (180) and capturing reflected and/or scattered light when said ear canal member is operationally mounted on the user.

The hearing aid system further comprises a sensor signal processing unit (170) that is connected to the surface electrode (150) and the light sensor (180) and that is configured to generate one or more sensor signals from each respective output signal of the at least one surface electrode (150) and the light sensor (180).

The hearing aid system further comprises or is connected to an evaluation unit (300) that is configured to generate an electrocardiogram-representing signal (ECG) from low voltage electric signals picked-up by the at least one surface electrode (150) and a plethysmographic-curve-representing signal from an output signal of the light sensor (180).

13 Claims, 11 Drawing Sheets

(51) Int. Cl.
  *A61B 5/352* (2021.01)
  *A61B 5/366* (2021.01)
  *A61B 5/0205* (2006.01)
  *A61B 5/00* (2006.01)
  *A61B 5/0295* (2006.01)
  *A61B 5/0285* (2006.01)
  *A61B 5/024* (2006.01)
  *A61B 5/287* (2021.01)
  *A61B 5/021* (2006.01)
  *A61B 5/11* (2006.01)
  *A61B 5/1455* (2006.01)

(52) U.S. Cl.
  CPC .............. *A61B 5/352* (2021.01); *A61B 5/366* (2021.01); *A61B 5/6817* (2013.01); *H04R 25/554* (2013.01); *H04R 25/558* (2013.01); *A61B 5/0285* (2013.01); *A61B 5/0295* (2013.01); *A61B 5/02125* (2013.01); *A61B 5/02416* (2013.01); *A61B 5/02427* (2013.01); *A61B 5/1102* (2013.01); *A61B 5/14552* (2013.01); *A61B 5/287* (2021.01); *A61B 2560/0223* (2013.01); *A61B 2562/0219* (2013.01); *H04R 2225/021* (2013.01); *H04R 2225/025* (2013.01); *H04R 2225/55* (2013.01)

(58) Field of Classification Search
  USPC .......................................................... 600/301
  See application file for complete search history.

(56) References Cited

U.S. PATENT DOCUMENTS

2017/0258329 A1    9/2017  Marsh
2019/0268706 A1*   8/2019  Solum ................. A61B 5/6815

* cited by examiner

HEARING AID SYSTEM

TECHNICAL FIELD

The invention refers to a hearing aid system comprising an audio signal input, an audio signal processing unit, an output transducer and an ear canal member that is configured to be placed in an ear canal of a human user.

BACKGROUND

Hearing instruments, such as hearing aids, are electro acoustic devices often used for enhancing sound by ways of amplification and modulation. A hearing instrument gathers sound from surroundings, amplifies the sound and directs the sound to ear canals of the user wearing the hearing instrument. For example, in case of a hearing impaired person, a hearing instrument may be configured to amplify sound coming from a frontal direction and cancel noise generated from all other audio signals, such that clear sound is perceived by the hearing impaired person, wearing the hearing instrument. The amplification and/or modulation are typically performed based upon a hearing profile of the hearing impaired person. Conventionally, hearing instruments are worn at or in a user's ear in a behind the ear (BTE) configuration, an in the ear (ITE) configuration, an in the canal (ITC) configuration, etc. Thus, hearing aids of a hearing aid system contact a user's skin in or next to the user's ear.

A hearing aid system may comprise one or more hearing instruments and optionally further devices or components. In particular, a hearing aid system may comprise remote components that are the at least temporarily wirelessly connected with one or more hearing instruments. The hearing instrument comprises an audio signal input, an audio signal processing unit, an output transducer and an ear canal member so as to allow processing of audio input signals and putting out a sound output signal that can be perceived as sound. The output transducer can be configured to convert an electric audio output signal into acoustic sound. Alternatively, the output transducer can be configured to convert an electric audio output signal into stimuli for stimulating the auditory nerve. The output transducer can be part of a cochlear implant of a hearing instrument.

The hearing instrument can comprise one or more microphones that provide an electric audio input signal to the audio input.

The hearing instrument can comprise further sensors for picking up physiological signals. Physiological signals are signals generated or originating from a human body, such as brainwave signals, electrocardiogram signals, heart rate signals, electroencephalogram signals, eye movements, iris diameter, skin conductivity, blood pressure etc.

Physiological signals can be processed to support fitting of a hearing instrument.

Remote components may comprise further processing devices for processing signals gathered or picked up by the hearing instrument.

Hearing aid systems that are configured to gather or pick up further physiological signals are inter alia disclosed in EP 2 744 224, EP2 950 555, EP 2 997 893 and EP 3 035 710.

SUMMARY

It is an object of the invention to provide a hearing aid system that provides additional benefit.

According to the invention, a first embodiment of the hearing aid system comprises an audio signal input, an audio signal processing unit, an output transducer and an ear canal member that is configured to be placed in an ear canal of a human user. The audio signal processing unit is operatively connected to the audio signal input. The audio signal processing unit is configured to process electric audio input signals and to generate electric audio output signals. The output transducer is operatively connected to the audio signal processing unit. The output transducer is configured to convert an electric audio output signal generated by the processing unit into a sound-representing output signal that can be perceived by the user as sound. The ear canal member comprises a sensor arrangement.

The hearing aid system further comprises a sensor arrangement comprising at least one surface electrode and a light sensor. The at least one surface electrode is located at a surface of said ear canal member to allow the electrodes to contact the skin of a user when the ear canal member is operationally mounted on the user. The at least one surface electrode is adapted to pick up a low voltage electric signal from the user's skin. The light sensor is located at a surface of the housing to allow emitting light through skin proximate to the light sensor and capturing reflected and/or scattered light when the ear canal member is operationally mounted on the user. The signals picked up or captured by the surface electrode and the light sensor are thus physiological signals or signals that can be processed so as to represent physiological signals. Physiological signals represent values of physiological parameters such as heart rate, blood pressure, electric potentials representing an electroencephalogram or an electrocardiogram, iris diameter, respiratory rate etc.

The hearing aid system further comprises a sensor signal processing unit that is connected to the surface electrode and the light sensor. The sensor signal processing unit is configured to generate one or more sensor signals from each respective output of the at least one surface electrode and the light sensor.

The hearing aid system further comprises or is connected to an evaluation unit. The evaluation unit is configured to generate an electrocardiogram-representing signal (ECG) from low voltage electric signals picked-up by the at least one surface electrode and a plethysmographic-curve-representing signal from an output signal of the light sensor.

The physiological signals generated by the hearing aid system can assist a healthcare professional to assess their decisions. This is beneficial because life expectancy is increasing and this puts higher demands on the healthcare sector because the elderly have higher healthcare needs. Continuous monitoring of the vital signs like respiratory rate or blood pressure by means of eHealth solutions can significantly contribute to detection and prevention of health problems. Today, healthcare professionals do not have online access to real-time measurements of vital signals to assess their decisions.

In a preferred embodiment, the evaluation unit is configured to determine one or more physiological parameter values, the physiological parameters comprise at least one of:

pre-ejection period (PEP) of a human heart cycle (indicator of cognitive effort/stress)

pulse transit time (PTT) (indicator of blood pressure) and/or heart rate (HR).

Preferably, the light sensor is a pulse oximeter.

A preferred hearing aid system further comprises an inertial sensor for sensing movements of the ear canal member when the ear canal member is operationally mounted on the user.

In an alternative embodiment, the hearing aid only comprises an inertial sensor in combination with a pick-up electrode but without an optical sensor. In the alternative embodiment, the hearing aid is configured to obtain a ballistocardiogram-representing signal (BCG) from an output signal of the inertial sensor and an electrocardiogram-representing signal (ECG) from low voltage electric signals picked-up by the at least one surface electrode.

In the alternative embodiment, the evaluation unit is configured to generate an electrocardiogram-representing signal (ECG) from low voltage electric signals picked-up by the at least one surface electrode and a ballistocardiogram-representing signal (BCG) from an output signal of the inertial sensor In both, the first and the alternative embodiment of the hearing aid system the inertial sensor can be a gyroscope.

In yet another alternative embodiment, the hearing aid system may comprise a gyroscope alone, without a light sensor or a pick-up electrode. It has been found that detecting cardiac parameters can be done merely by a gyroscope mounted on the ear which provides angular deflections due to the periodic heart rhythm.

In any embodiment, the hearing aid system may preferably further comprise a behind the ear part that comprises a further surface electrode located at a surface of the behind the ear part to allow the further electrode to contact the skin of a user when the behind the ear part is operationally mounted on the user. The further surface electrode is adapted to pick up a low voltage electric signal from the user's skin.

In a preferred embodiment, the hearing aid system comprises at least one hearing instrument that comprises the audio signal input, the audio signal processing unit, the output transducer and the ear canal member that comprises the sensor arrangement.

It is further preferred if the hearing aid system comprises two hearing instruments, each hearing instrument comprising at least one surface electrode.

The hearing instrument preferably comprises the in-the-ear part and the behind-the-ear part, wherein the in-the-ear part comprises the ear canal member that comprises the at least one surface electrode and wherein the behind-the-ear part comprises a further surface electrode.

The hearing instrument preferably further comprises a memory unit and a wireless data interface that is operatively connected to said memory unit.

Preferably, the hearing instrument is configured to wirelessly communicate with the evaluation unit via the wireless data interface.

According to a further aspect a method for monitoring values of a physiological parameter is provided, wherein the method comprises:

picking up physiological signals by means of a sensors arranged on or in a hearing instrument, said sensors comprising at least one of a surface electrode, a light sensor and/or an inertial sensor, processing said physiological signals and generating one or more sensor signals from each respective output signal of said sensors, and evaluating said sensor signals to generate at least one of an electrocardiogram-representing signal (ECG) from low voltage electric signals picked-up by said at least one surface electrode (150), a plethysmographic-curve-representing signal from an output signal of said light sensor (180), and/or a ballistocardiogram-representing signal (BCG) from an output signal of said inertial sensor (240).

Preferably the method further comprises a step of determining values representing a duration of a pre-ejection-period (PEP). Additionally or alternatively, the method may further comprise a step of determining values representing a duration of a pulse-transit-time (PTT). In particular, the method can further comprise a step of determining values representing blood pressure.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
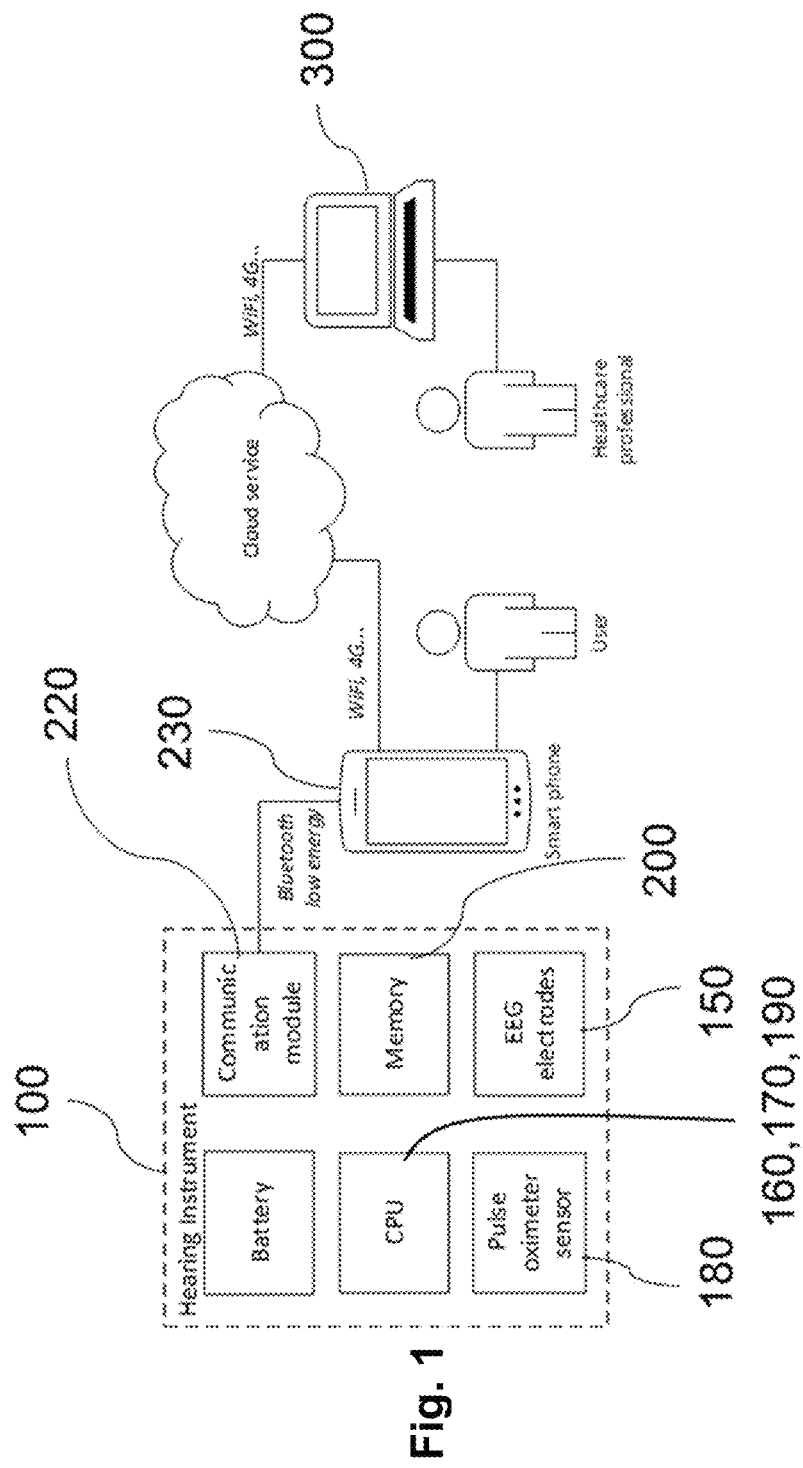
FIG. 1: illustrates a hearing aid system according to the first embodiment.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals or with a receiver/loudspeaker arranged close to or in the ear canal such as in a Behind-the-Ear type hearing aid or a Receiver-in-the Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A hearing device may be part of a "hearing system", which refers to a system comprising one or two hearing devices, disclosed in present description, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follows.

FIG. 1 illustrates a hearing aid system that allows a continuous measurement of the PEP by using a hearing instrument capturing physiological signals from sensors in the ear canal. The main idea behind this invention is to measure the PEP rate using two different sensors: light sensors (pulse oximeter sensors) and electric sensors (electrodes).

The system shown in FIG. 1 additionally or alternatively uses a hearing instrument that provides a non-intrusive and continuous measurement of blood pressure from the ear canal. This embodiment is based on the Pulse-Transit-Time method. The main idea behind this method is to measure heart rate using two different sensors: a light sensor (pulse oximeter sensor) and an electric sensor (electrode). From the existing time-shift between these two captured signals (due to physiological reasons), it is possible to derivate the blood pressure. This method has been used to estimate blood pressure from the fingertip [M. Asif-Ul-Hoque, Md. Sabbir Ahsan, and Bijoy Mohajan. 2011. Measurement of Blood Pressure Using Photoplethysmography. In 2011 UkSim 13$^{th}$ International Conference on Computer Modelling and Simulation, 32-35.]

FIG. 1 provides an overview of the envisioned system (the dotted-line box delimits the system). The system comprises a hearing instrument 100 that has two sensors 150 and 180 that gather signals from the ear canal: a light sensor, i.e. a pulse oximeter sensor 180 and an EEG electrode 150. The EEG electrode 150 requires an additional electrode (not shown) to be used as reference; this reference electrode can be obtained from the hearing instrument in the other ear or alternatively two electrodes can be placed in the same ear. The signals of both sensors 150 and 180 are processed by a CPU unit that implements an electrode sensor signal conditioning unit 160 and a light sensor signal conditioning unit 190 that are configured to eliminate noise (e.g., bandpass filtering). The CPU unit further implements a sensor signal processing unit 170 that is configured to obtain the desired heart beat measurements. Signals from both sensors 150 and 180 need to be time synchronized (e.g., using the same hardware platform or through an external trigger).

According to a first aspect, the PEP value is stored in a memory 200 and can send to a smart phone 230 or other personal mobile device of the user of the hearing instrument 100 through a communication module 220 of the hearing instrument 100, e.g. using a Bluetooth low energy communication module. Preferably, the user can allow his or her PEP value representing data to be shared with third parties (e.g., healthcare professional) through a cloud service via his or her smart phone or other personal mobile device. An evaluation unit 300 can be connected to the smartphone 230 and/or the hearing instrument via a one or more data networks also called "cloud" or internet.

According to a second aspect of the first embodiment that can be combined with the first aspect or can be implemented independently from the first aspect, both sensor signals are evaluated to determine a point of time that relates to a respective pulse corresponding to a heartbeat. The time-shift between the pulses in both sensor signals, i.e. the pulse transit time (PTT) is used to determine the blood pressure value at a certain point in time. The blood pressure value is stored in memory 200 and can be send to the smart phone 230 or other personal mobile device of the user of the hearing instrument 100 through a communication module 220, e.g. a communication module using Bluetooth low energy. Preferably, the user can allow his or her blood pressure representing data to be shared with third parties (e.g., healthcare professional) through a cloud service. An evaluation unit 300 can be connected to the smartphone 230 and/or the hearing instrument via a one or more data networks also called "cloud" or internet.

Figure 2:
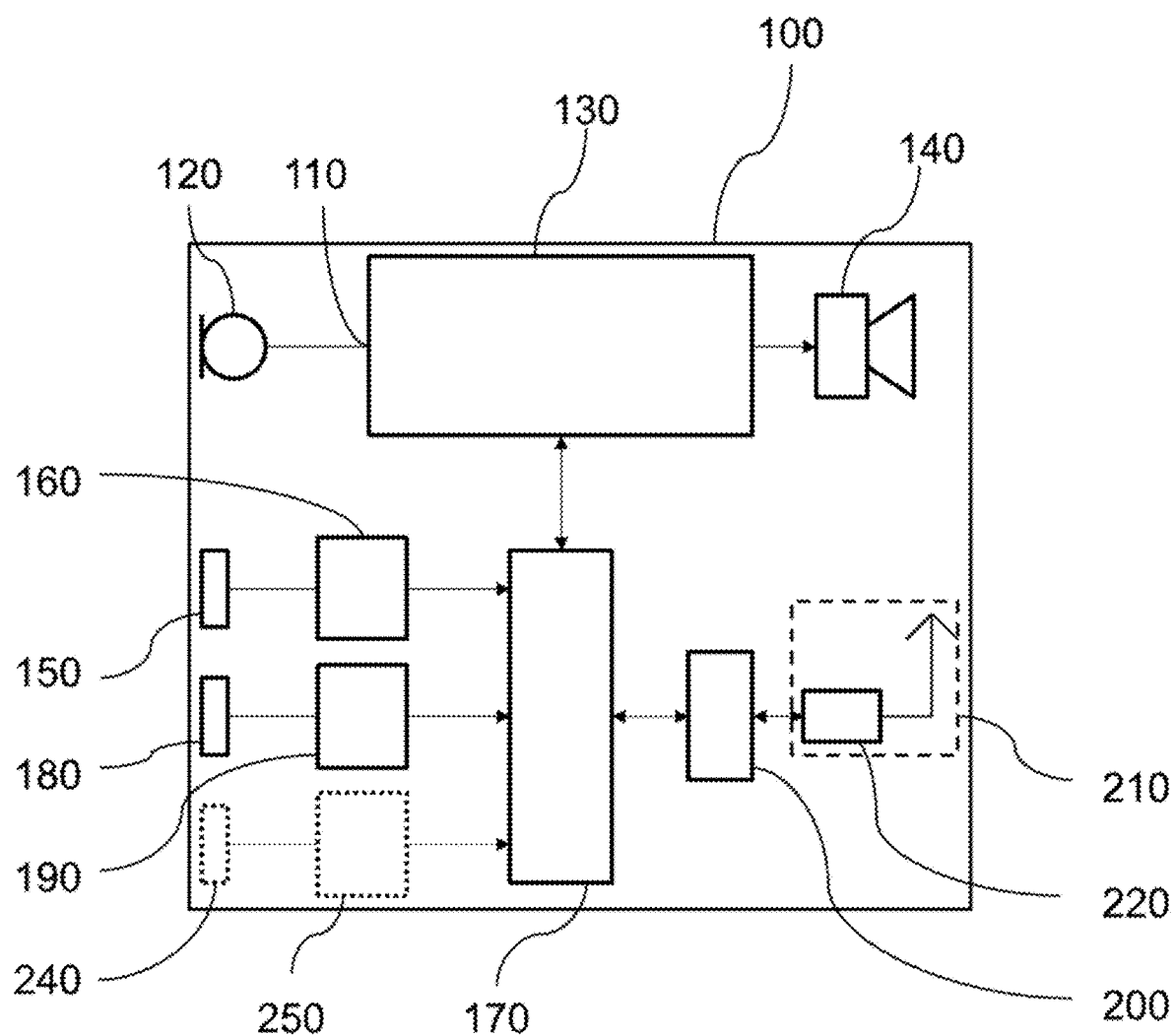
FIG. 2: illustrates a schematic block diagram of a hearing instrument of a hearing aid system according to the first embodiment.

FIG. 2 illustrates a hearing instrument 100 for use in a hearing aid system according to FIG. 1. The hearing aid instrument 100 comprises a signal input 110 that is connected to an output of a microphone 120 and microphone 120 is an input transducer that converts acoustic sound into an electric input audio signal. Signal input 110 could alternatively be connected to a receiver or other means for receiving an electric input audio signal. Signal input 110 is connected to an audio signal processing unit 130 that is configured to process the electric audio input signal and to generate an electric audio output signal according to the needs of a user. The electric audio output signal is fed to an output transducer 140 that is configured to convert the electric audio output signal into a sound-representing output signal that can be perceived by the user as sound. The output transducer 140 can be a speaker (receiver) or a stimulation unit for stimulating the auditory nerve.

According to the invention, the hearing instrument 100 further comprises one or more surface electrodes 150 for picking up low voltage signals from the skin of a user. The surface electrode 150 is connected to a signal conditioning unit 160 that is configured to amplify and filter the electric signal picked up by the surface electrode 150. The preconditioned signal is fed to a sensor signal processing unit 170 that is configured to generate one or more sensor signals from the output of the at least one surface electrode.

Hearing instrument 100 further comprises a light sensor 180 that is configured as a pulse oximeter sensor. The pulse oximeter sensor is a sensor that emits light through the skin and that senses light reflected or scattered from a user's body. The pulse oximeter signal is fed to a second signal conditioning unit 190 that in turn provides a conditioned oximeter signal to the sensor signal processing unit 170. Sensor signal processing unit 170 is further configured to generate a sensor signal from the output signal of light sensor 180.

Sensor signal processing unit 170 is connected to audio signal processing unit 130. Further, sensor signal processing unit 170 is connected to a memory unit 200. Memory unit 200 is configured to store data either provided by sensor signal processing unit 170 or received via a wireless data interface 210 or both.

The hearing aid system according to FIGS. 1 and 2 further comprises an evaluation unit that is wirelessly connected to the hearing instrument 100 by means of the wireless data interface 210. Wireless data interface 210 comprises a communication module 220 that is configured to wirelessly communicate with a portable mobile device such as a Smart phone 230 via a known wireless data transmission protocol such as Bluetooth low energy. Smart phone 230 is a relay system that can connect to the internet and via the internet to a remote evaluation unit 300.

In a preferred embodiment, the hearing instrument 100 further comprises an inertial sensor 240, i.e. a gyroscope or other inertial motion unit (IMU), that is configured so it can capture periodic motions arising from the sudden ejection of blood into the aorta—also known as Ballistocardiogram signal. A further signal conditioning unit 250 may be provided to condition the inertial sensor output signal so it can be processed by the sensor signal processing unit 170.

Figure 3:
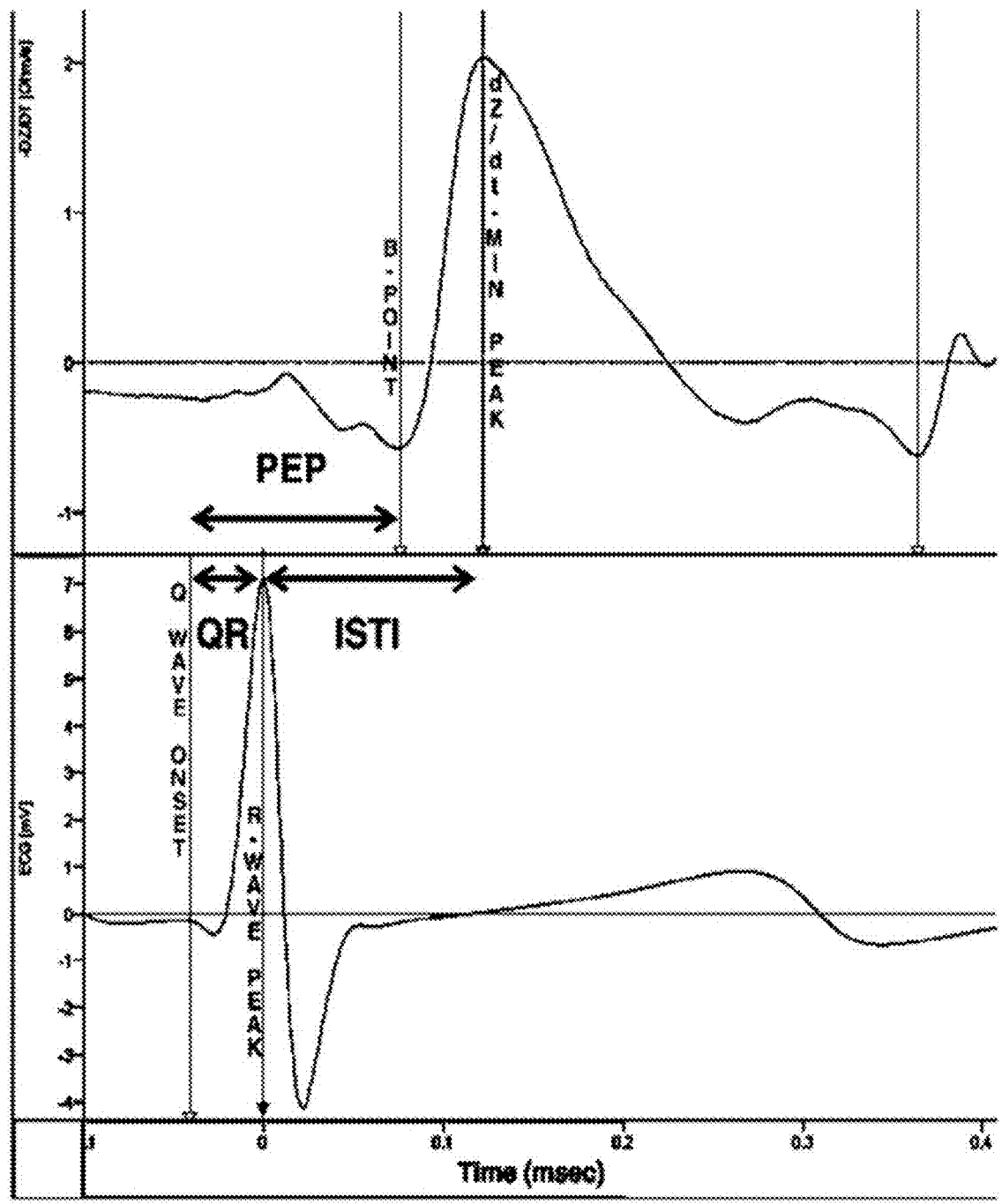
FIG. 3: illustrates an impedance cardiogram (top) and an electrocardiogram (bottom) with four landmarks defining the PEP (Q-wave onset to B-point) and the ISTI (R-peak to dZ/dt-min peak)

FIG. 3 illustrates how to obtain a signal that represents the duration of the Pre-Ejection Period (PEP) by means of a surface electrode cardiogram (ECG) signal and a light sensor pulse oximeter signal. [Rene van Lien, Nienke M. Schutte, Jan H. Meijer, and Eco J. C. de Geus. 2013. Estimated preejection period (PEP) based on the detection of the R-wave and dZ/dt-min peaks does not adequately reflect the actual PEP across a wide range of laboratory and ambulatory conditions. International Journal of Psychophysiology 87, 1: 60-69.]

The initial systolic time interval (ISTI) reflects a time difference between the electrical and pumping activity of the heart and depends on cardiac preload, afterload, autonomic nervous control and training level [Maureen A. J. M. van Eijnatten, Michael J. van Rijssel, Rob J. A. Peters, Rudolf M. Verdaasdonk and Jan H. Meijer, Comparison of cardiac time intervals between echocardiography and impedance cardiography at various heart rates; J Electr Bioimp, vol. 5, pp. 2-8, 2014]. ISTI can be measured by determining the R-peak to dZ/dt-min peak interval.

The signals captured by the embodiment according to FIGS. 1 to 3 can be used in several use cases, like allowing the user to do self-monitoring on PEP measurements and/or share those with healthcare professional through a cloud service thus enabling remote monitoring by a professional. More interestingly, we believe that there may be a correlation between PEP measurements and listening effort. This would enable to use this PEP measurements to change hearing instrument settings thus enabling an objective and personalized bio feedback. This could be implemented in a simple rule-based model like shown below:

```
if PEP < Personal_threshold:
    Listening effort acceptable -> Keep hearing instrument settings
else:
    Too high a listening effort -> Change hearing instrument settings
```

Figure 4:
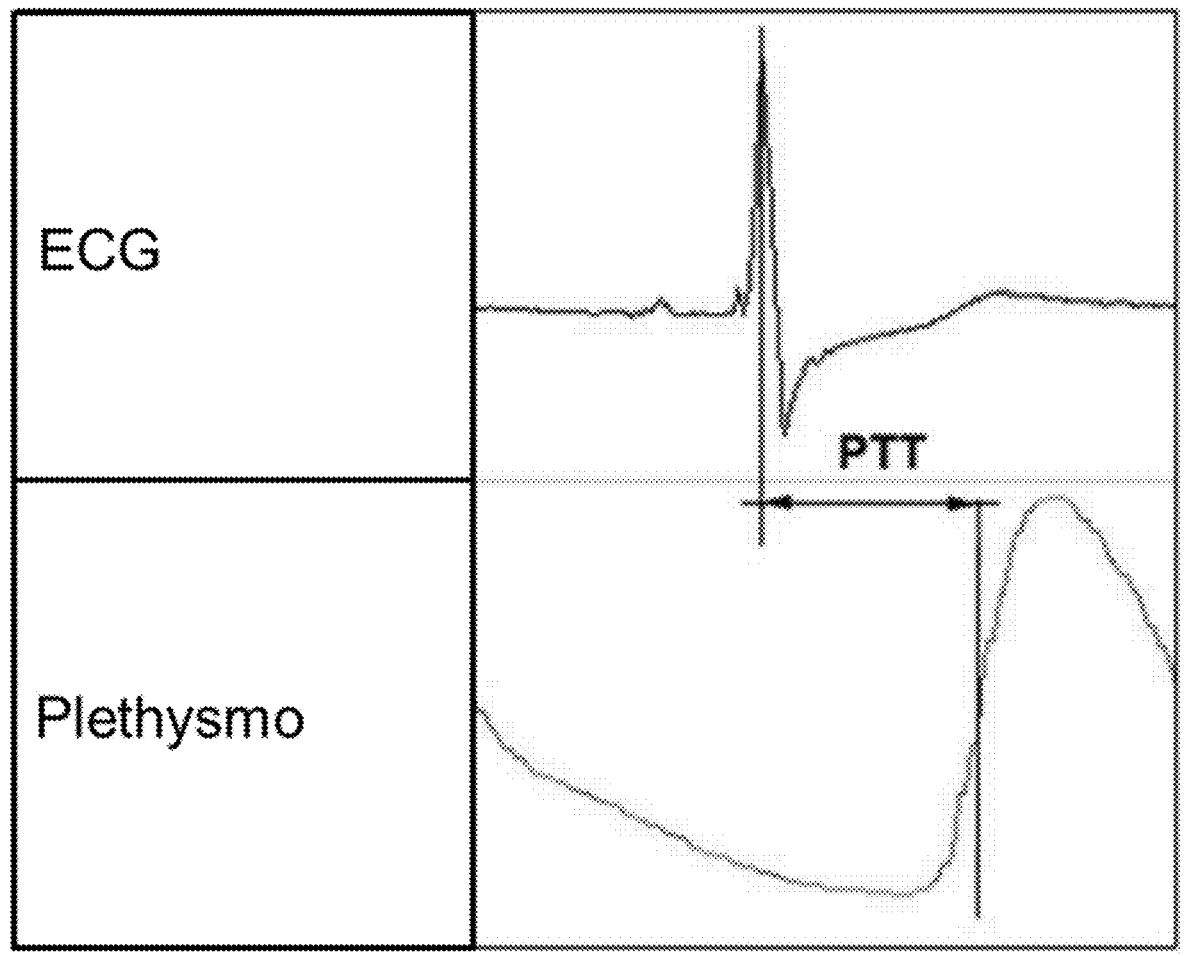
FIG. 4: illustrates calculating the Pulse-Transit-Time by measuring the time delay between the heart beat measured from electrodes and pulse-oximetry.

FIG. 4 illustrates how the Pulse-Transit-Time (PTT) is calculated as the time difference between the heart beat seen from the electrode signal and the pulse-oximetry sensor. This PTT value is then used to estimate the blood pressure using a lineal or non-lineal (different methods used in literature). This usually requires some calibration process that consists on providing (at least) one reference measurement [Heiko Gesche, Detlef Grosskurth, Gert Küchler, and Andreas Patzak. 2012. Continuous blood pressure measurement by using the pulse transit time: comparison to a cuff-based method. European Journal of Applied Physiology 112, 1: 309-315]. This calibration process would require to measure blood pressure using a golden standard system (e.g., sphygmomanometer) and feed the measured value to the system (using the smart phone as an interface). This calibration process will only need to be done once.

The hearing aid system according to the second aspect can be used in several use cases. It allows the user of the device to self-monitor their blood pressure in different situations. The invention also offers the possibility to set alarms when acute, hazardous blood pressure levels are reached. Moreover, blood pressure time series can be shared with a healthcare professional through a cloud service enabling remote monitoring by a professional. Last but not least, this invention offers a unique opportunity to analyse the associations of hearing loss performance and a physiological measure like blood pressure. This associations can potentially be used to fine-tune hearing aid settings.

Figure 5:
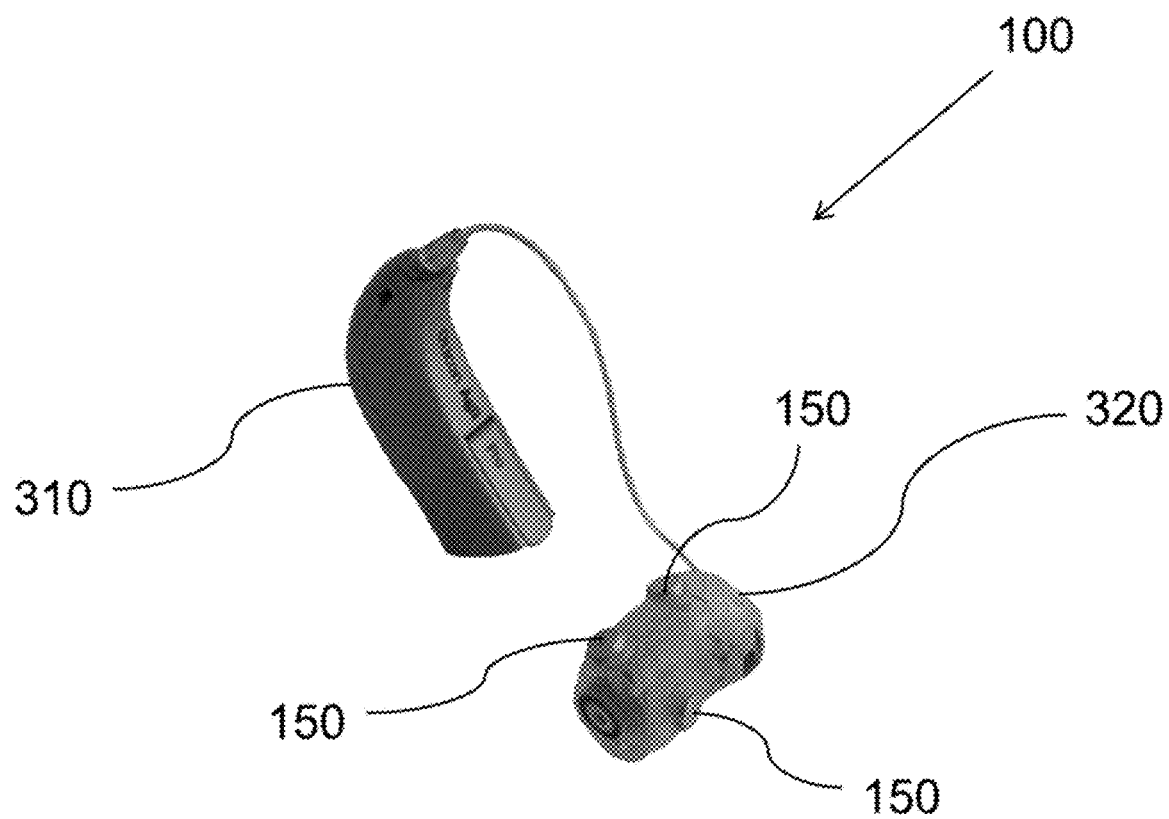
FIG. 5: illustrates a hearing aid with EEG electrodes and a pulse oximeter sensor.

FIG. 5 illustrates a hearing instrument with EEG electrodes used to obtain an electrocardiogram signal (ECG) and pulse oximeter sensor to obtain a plethysmogram signal.

Figure 6:
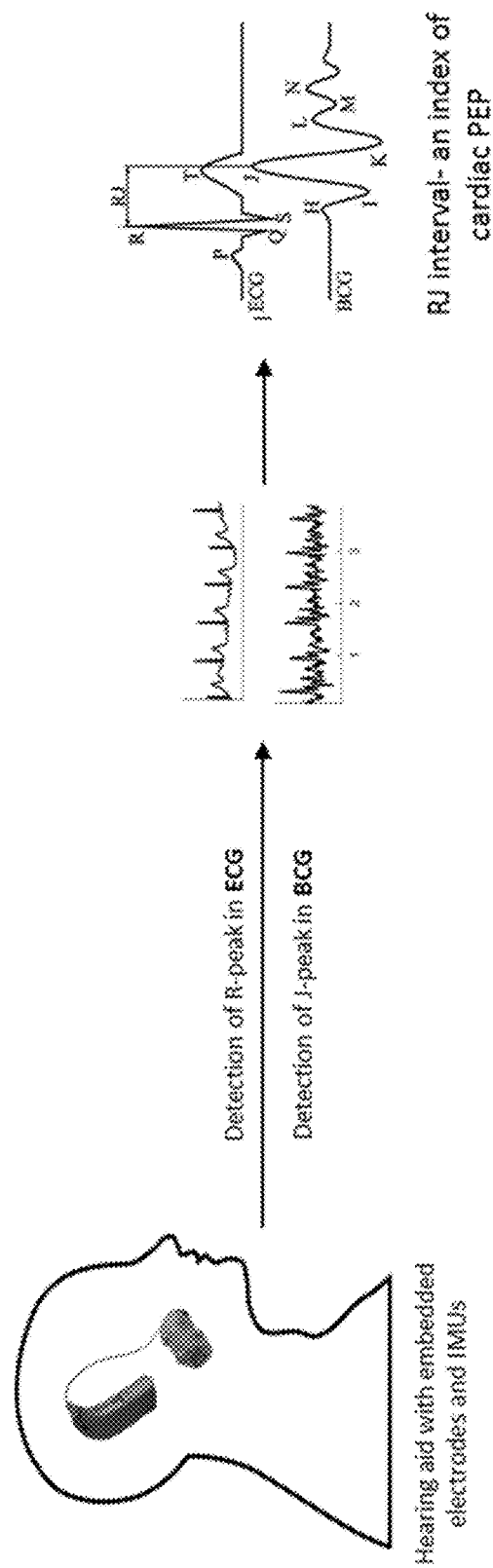
FIG. 6: illustrates an on ear measurement of RJ interval as an index of sympathetic activity.
Figure 7:
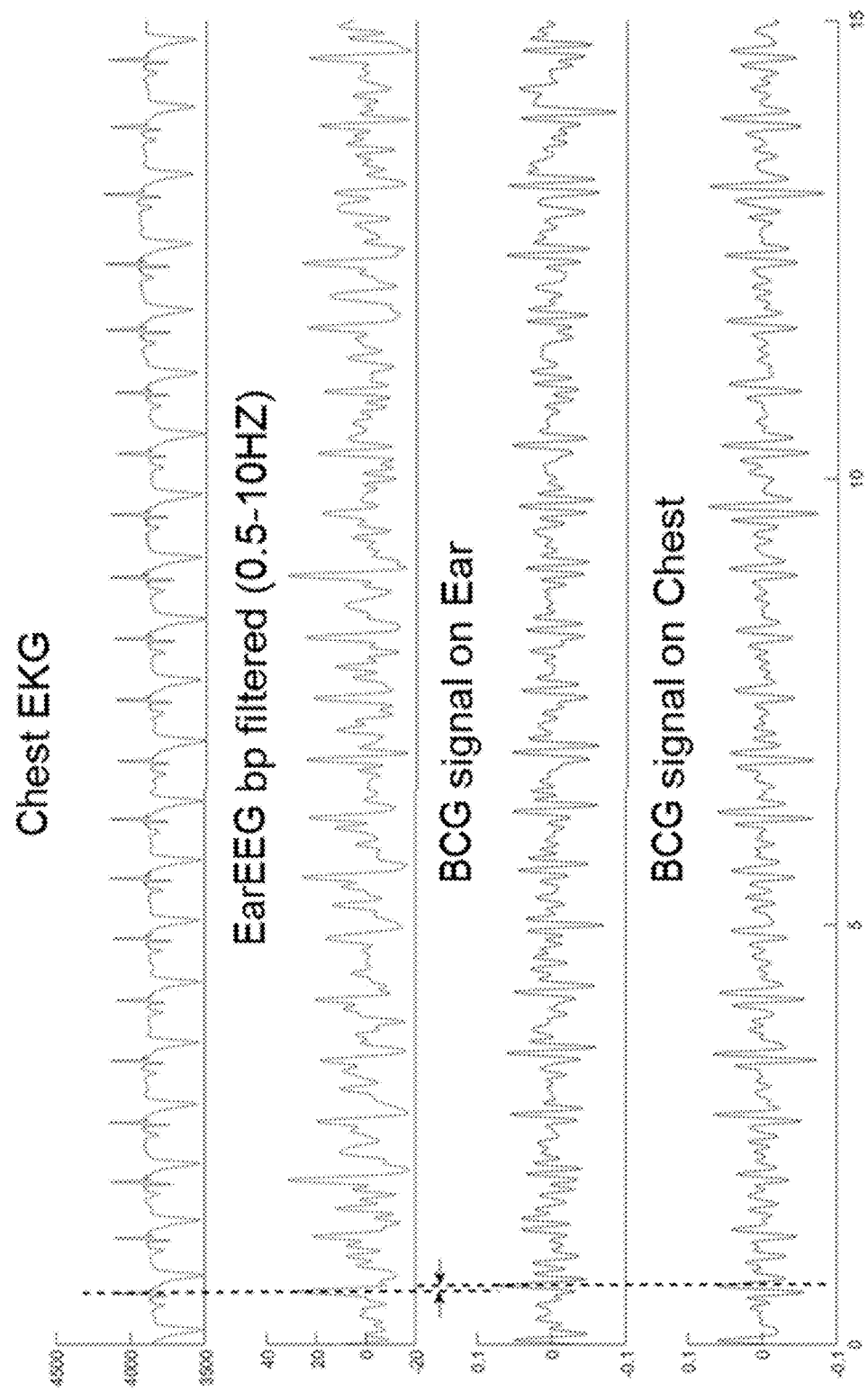
FIG. 7: shows an excerpt of recording with the above mentioned setting.
Figure 8:
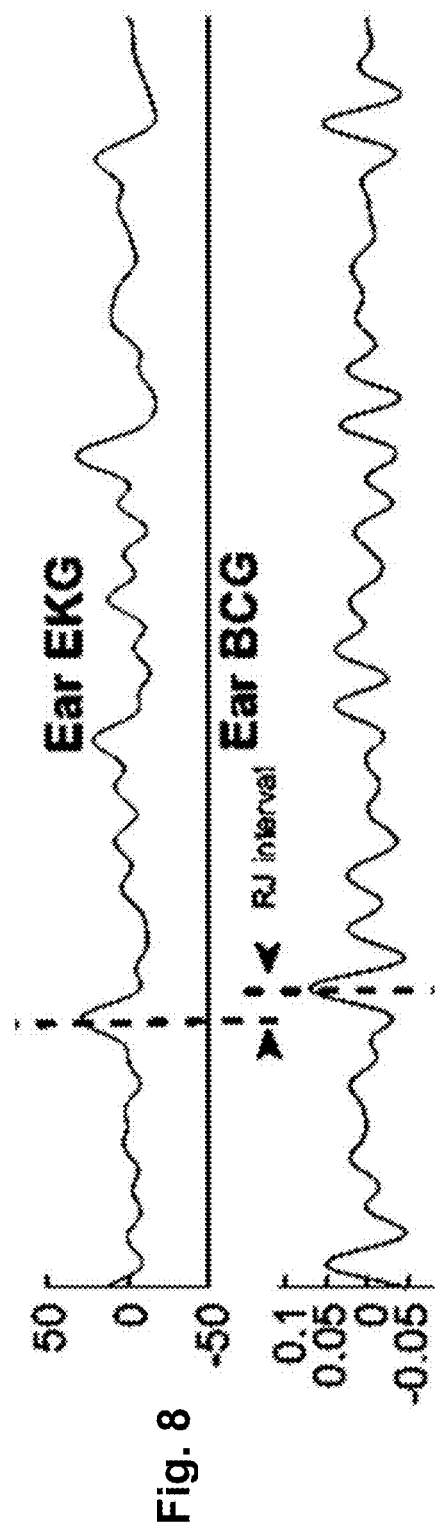
FIG. 8: shows a zoomed segment of ear level recording.

In FIGS. 6, 7 and 8, an alternative embodiment providing a method of sympathetic measure based on a cardiac signal is presented. As the cardiac output rate is controlled by both sympathetic and parasympathetic branch of the autonomic nerve system (ANS), therefore, the heart rate itself is not a robust marker for capturing the sympathetic activity. Several time and frequency domain methods can be used to extract the pure sympathetic activity of heart—which is in other way, a measure for cognitive effort.

The alternative embodiment provides non-invasive method of monitoring effort measure in terms of pre-ejection-period (PEP), which has been identified as a pure measure of sympathetic effect on heart—in other words, a measure of cognitive effort.

The sympathetic effect on the heart is prominent in the time period between the start of the ventricular contraction occurs and the opening of the aortic valves; the time duration is defined as PEP. An ear level measurement of PEP can be therefore of significant importance to capture HA user's instantaneous cognitive effort.

The PEP can be measured by simultaneous recording of either ECG and Thoracic impedance (ICG) or ECG and Ballistocardiograph (BCG) signal. The former requires a special setup with a sinusoidal current of ~50 kHz to measure the change in impedance during the ventricular contraction. However the later method using an ECG signal and a BCG signal is non-invasive and requires only a pair of electrodes to capture ECG and an inertial sensor to capture the heart movement via the ballistocardiogram. Based on the later setup, an ear level sympathetic measurement incorporating ECG and BCG signals is provided.

The hearing aid system for ear level PEP measurement comprises in-ear electrodes and an inertial sensor mounted on ear.

The basic set-up is:
An ear level device with embedded inertial sensor
In ear electrodes that capture the ECG artifacts (crossed referenced).
Embedded algorithm to estimate the PEP.

Accordingly, according to the alternative embodiment, a hearing aid system for ear level PEP measurement is provided that comprises an audio signal input, an audio signal processing unit, an output transducer and an ear canal member that is configured to be placed in an ear canal of a human user. The audio signal processing unit is operatively connected to the audio signal input. The audio signal processing unit is configured to process electric audio input signals and to generate electric audio output signals. The output transducer is operatively connected to the audio signal processing unit. The output transducer is configured to convert an electric audio output signal generated by the processing unit into a sound-representing output signal that can be perceived by the user as sound. The ear canal member comprises a sensor arrangement.

The hearing aid system according to the alternative embodiment further comprises a sensor arrangement comprising at least one surface electrode and inertial sensor. The at least one surface electrode is located at a surface of the ear canal member to allow the electrodes to contact the skin of a user when the ear canal member is operationally mounted on the user. The at least one surface electrode is adapted to pick up a low voltage electric signal from the user's skin. The inertial sensor is located in the hearing instrument so it can capture periodic motions arising from the sudden ejection of blood into the aorta—also known as Ballistocardiogram signal. The signals picked up or captured by the surface electrode and the inertial sensor are thus physiological signals or signals that can be processed so as to represent physiological signals. Physiological signals represent values of physiological parameters such as heart rate, blood pressure, electric potentials representing an electroencephalogram or an electrocardiogram, iris diameter, respiratory rate etc.

The hearing aid system according to the alternative embodiment further comprises a sensor signal processing unit that is connected to the surface electrode and the inertial sensor. The sensor signal processing unit is configured to generate one or more sensor signals from each respective output of the at least one surface electrode and the inertial sensor.

The hearing aid system according to the alternative embodiment further comprises or is connected to an evaluation unit. The evaluation unit is configured to generate an electrocardiogram-representing signal (ECG) from low voltage electric signals picked-up by the at least one surface electrode and a ballistocardiogram-representing signal (BCG) from an output signal of the inertial sensor.

Basically, the signal provided by the ear electrodes, ie. the surface electrodes meant for recording EarEEG has artifact of heart beats which is correlated to the ECG captured on the standard configuration. In addition to this, the inertial sensor, i.e. an inertial motion unit (IMU), is mounted on the ear. The inertial sensor can capture the periodic motions of human body arising from the sudden ejection of blood into the aorta, i.e. a Ballistocardiogram signal. The duration between the peak of ECG (R-peak) and the peak of the BCG (J-peak) is an estimation of PEP which is actually the measure of sympathetic activity. The duration between the peak of ECG (R-peak) and the peak of the BCG (J-peak) is called RJ-interval in this disclosure.

Ear level effort measurement can be an estimate of the hearing aid users' cognitive ability and therefore can provide biofeedback for various purposes—ranging from monitoring to the cognitive control of hearing aid.

Human's cognitive ability can be explicated by the Autonomic Nervous System (ANS) [Zygmunt, A., & Stanczyk, J. Methods of evaluation of autonomic nervous system function. *Archives of Medical Science: AMS*, 6(1), 11-18, 2010]. The ANS has two different branches—Sympathetic Nervous System (SNS) and Parasympathetic Nervous System (PNS). The sympathetic part is responsible for increased effort and stress while the parasympathetic part accounts for relax/calm state. Influences of ANS is latent in various physiological states, e.g. heart rate, pupil dilation, galvanic skin resistance etc.

Although the physiological signals concomitant with the above mentioned physiological states can be used to effort measurements, of ear level measurements of such signals in view to having real time feedback are not used in the prior art. It is noted that with respect to ear level measurement of the signal reflecting ANS activity, additional circuitry, i.e. signal conditioning means implemented in hardware may be provided.

FIGS. 7 and 8 present an example of the on-ear setup of capturing PEP measurement. The subject was at rest (leaning on the chair). In ear electrodes were placed to capture the ECG signal and an IMU sensor was mounted on the ear level. To benchmark the recorded signal at the ear level, a single lead ECG at chest was also recorded (Lead 1) and another IMU sensor was placed at the sternum.

FIG. 6 illustrates on ear measurement of RJ interval (the duration between the peak of ECG (R-peak) and the peak of the BCG (J-peak)) as an index of sympathetic activity.

FIG. 7 is an excerpt of recording with the above mentioned setting. It is prominent that the chest ECG and the ECG recorded from the ear are correlated. Similarly BCG signal captured from both on the chest and ear is correlated. The delay between ECG and BCG is same as recorded both from chest and on the ear level.

FIG. 8 is a zoomed segment of ear level recording. The RJ interval can be clearly measured from ear level recording as is an estimation of PEP and sympathetic activity.

The embodiment of FIGS. 6, 7 and 8 presents a measurement of the emotional effort incorporating heart signal captured from ear level sensors. With this simple but effective approach, additional embedded circuitry is not needed when compared to other developed technology like pulse-oximetry.

The measurement of sympathetic activity on the ear level can provide manifold advantages. This provides a useful feedback control to hearing devices when listening becomes effortful for the device user as well as other cardiac parameters can be estimated for remote monitoring of users.

Figure 9:
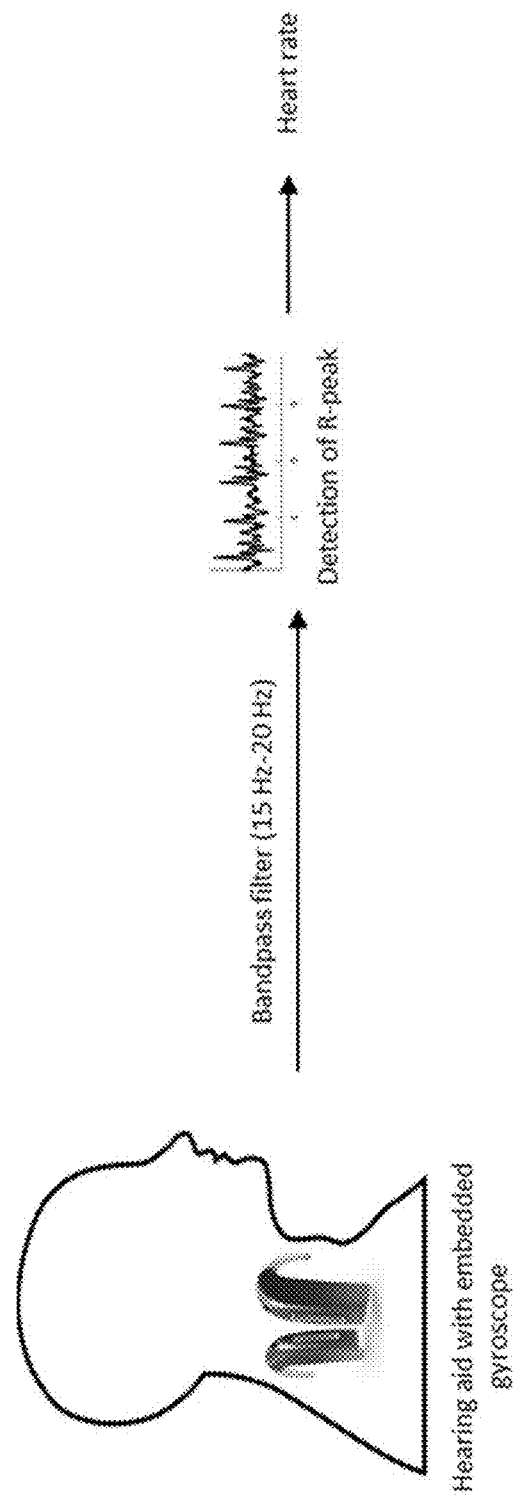
FIG. 9: illustrates heart rate detection using a gyroscope embedded hearing aid.
Figure 10:
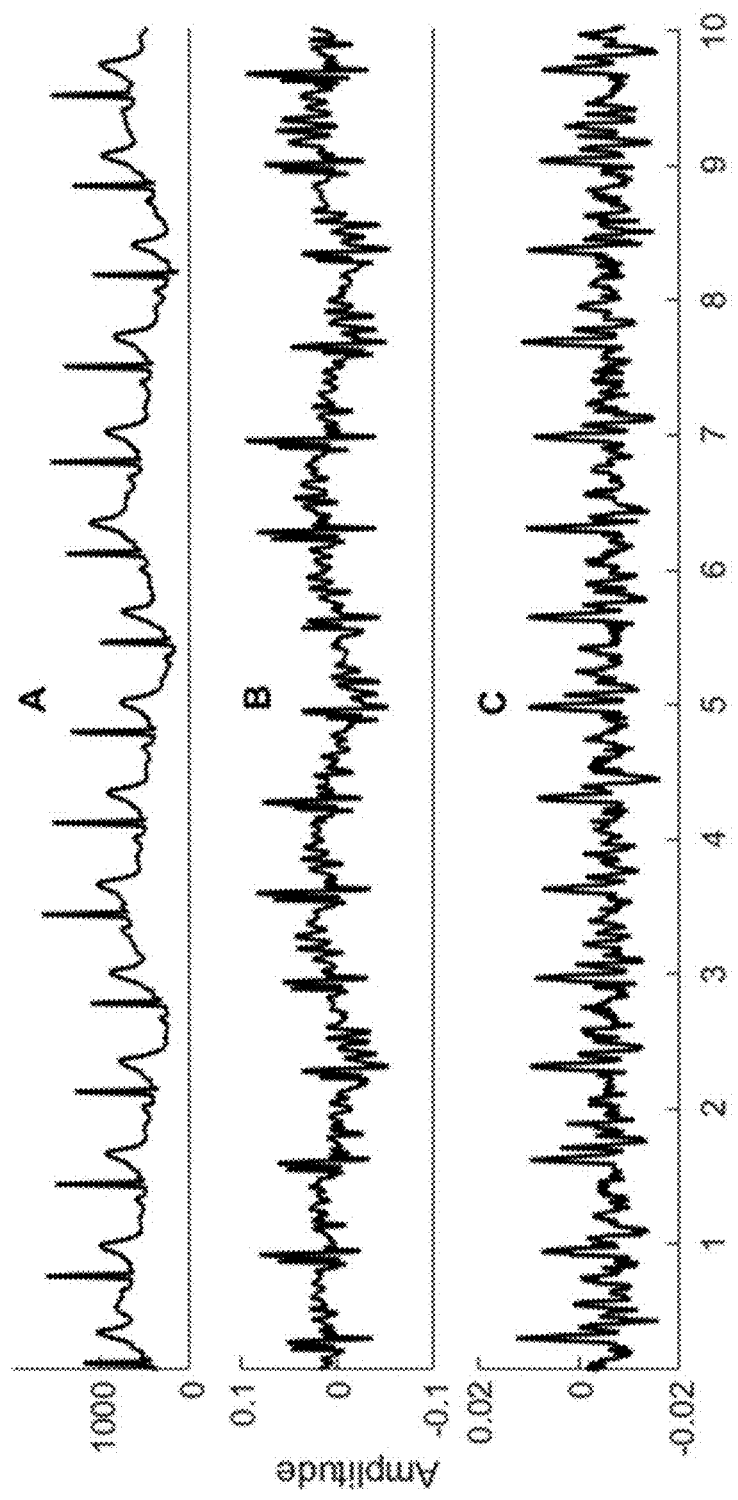
FIG. 10: illustrates simultaneous recording of an ECG signal (A), a BCG signal captured by a gyroscope (B) and a chest and on the ear (C)
Figure 11:
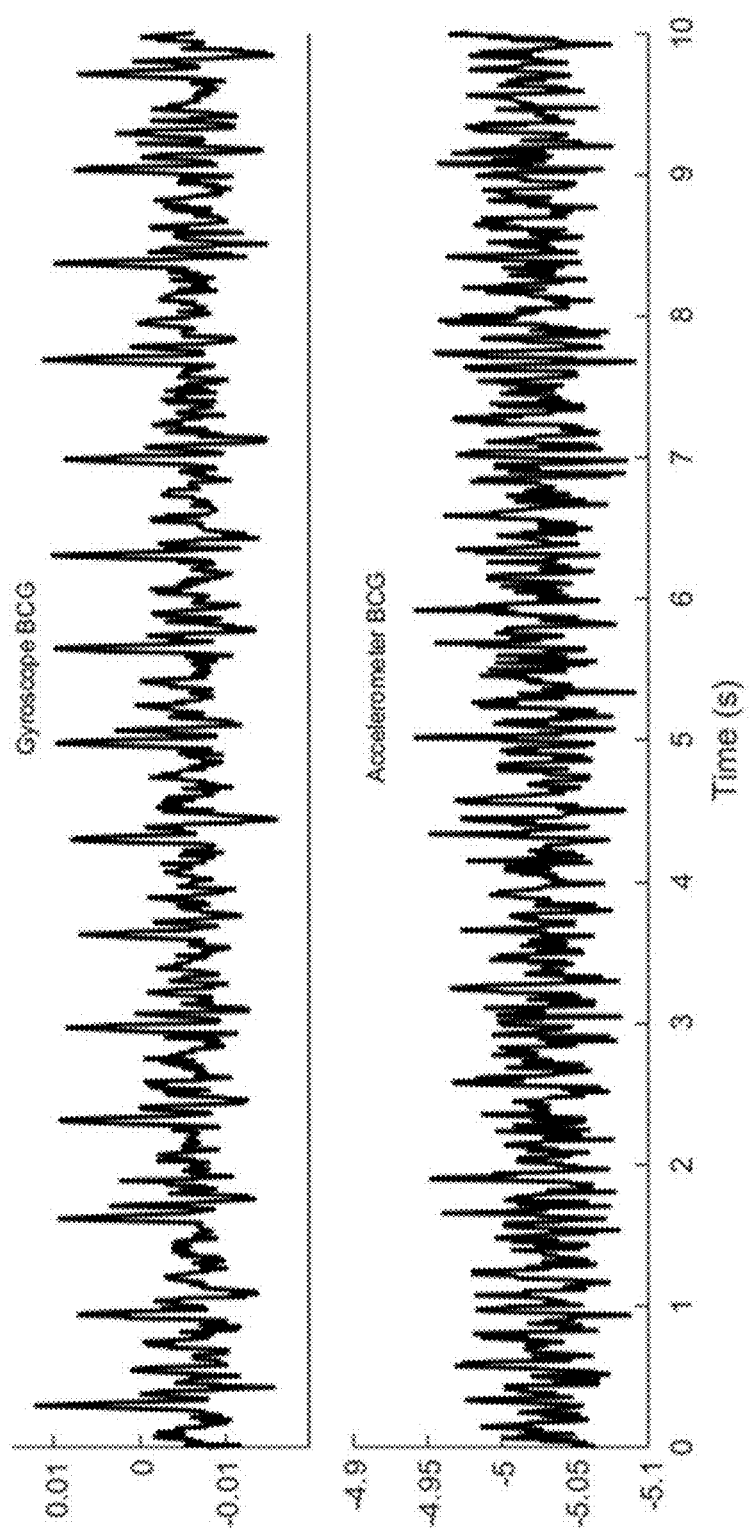
FIG. 11: illustrates simultaneous recording of BCG data from accelerometer and gyroscope on the ear.

FIGS. 9, 10 and 11 illustrated yet another alternative embodiment of a hearing aid system implementing a non-invasive method of monitoring heart rate using inertial sensors embedded with gyroscope at the level of the ear (as an embedded tool in an ear-level device such as a hearing aid, a cochlear implant, or a communication device, commonly referred to as hearing instrument). The sensor is mounted for other significant purposes like estimation of directionality etc. where the measurement of heart rate is a significant outcome of it.

The periodic heart vibration is propagated to the body which the highly sensitive gyroscope captures. This measurement can be used to monitor heart rate. The ear-level inertial sensors provide significant advantage over wristband wearables in terms of stability. Ear-level inertial sensors enable to record heart rate on hearing device users with no extra mounting of other biosensors.

Detecting cardiac parameters can be done merely by a gyroscope mounted on the ear which provides angular deflections due to the periodic heart rhythm.

The base of this setup is:

An ear-level device embedded with gyroscope as an inertial sensor

Bandpass filtering of Ballistocardiograph (BCG) signal captured by the gyroscope Embedded algorithm to detect the R-peak of BCG signal to report the heart rate.

Accordingly, according to the second alternative embodiment, a hearing aid system is provided that comprises an audio signal input, an audio signal processing unit, an output transducer and an ear canal member that is configured to be placed in an ear canal of a human user. The audio signal processing unit is operatively connected to the audio signal input. The audio signal processing unit is configured to process electric audio input signals and to generate electric audio output signals. The output transducer is operatively connected to the audio signal processing unit. The output transducer is configured to convert an electric audio output signal generated by the processing unit into a sound-representing output signal that can be perceived by the user as sound. The ear canal member comprises a sensor arrangement.

The hearing aid system according to the second alternative embodiment further comprises a gyroscope. The gyroscope is located in the hearing instrument so it can capture periodic motions arising from the sudden ejection of blood into the aorta—more known as Ballistocardiogram signal. The signal picked up or captured by the gyroscope thus is a physiological signal or a signal that can be processed so as to represent a physiological signal, i.e. a ballistocardiogram representing the heart rate.

The hearing aid system according to the second alternative embodiment further comprises a sensor signal processing unit that is connected to the gyroscope. The sensor signal processing unit is configured to generate a sensor signal from the output of the gyroscope.

The hearing aid system according to the second alternative embodiment further comprises or is connected to an evaluation unit. The evaluation unit is configured to generate a ballistocardiogram-representing signal (BCG) from an output signal of the gyroscope.

FIG. 9 illustrates heart rate detection using a gyroscope embedded in a hearing instrument.

FIG. 10 presents an example of ear-level heart rate monitoring. The subject was at rest (in sitting position) while the gyroscope embedded inertial sensor was mounted on ear-level and on the chest. To benchmark the recorded signal, a single lead Electrocardiogram (ECG, lead I) was recorded simultaneously. In particular, FIG. 10 illustrates the simultaneous recording of ECG signal (A), BCG signal captured by gyroscope at Chest (B) and on the Ear (C). It can be seen that the BCG signal captured on the chest is similar to the signal captured on the ear. The peaks of the BCG signal can be used to estimate the heart rate when compared to the ECG signal.

The BCG signal detected by the gyroscope and the simultaneous recording of the ECG has been presented in FIG. 2. The peaks of the ECG signal (R-peak) correlates with the peak of BCG signal (J-peak) which apparently provides the instantaneous heart rate.

FIG. 11 provides the traditional BCG recording by accelerometer on ear. It can be seen that the signal quality is better in gyroscope than the accelerometer mounted on the ear and that the accelerometer data is noisier than the gyroscope BCG data.

In case of induced motion artifact, the heart rate variability can be captured by using 10 seconds average beats which is clinically relevant measure for monitoring.

Monitoring the cardiac performance has been one of the primary focuses of wearable devices. With the approach illustrated in FIGS. 9, 10 and 11, the heart rate can be monitored with the embedded inertial sensors which are mounted at ear-level for broader applications. The BCG signal captured by the embedded gyroscope can provide telehealth monitoring of elderly people who already use ear-level devices. With this simple but effective approach, additional embedded circuitry is not needed when compared to developed technology like pulse-oximetry.

In addition to this, heart rate variability can be used to study the sympathetic and parasympathetic activity which has been found to be correlated with the listening effort (Tietz et al 2017). This provides a useful feedback control to hearing devices when listening becomes effortful for the device user.

The use of inertial sensors at the level of the ear can also serve additional purposes beyond electrocardiographic measurement, e.g. interacting with a hearing device like increasing its volume or steering its directionality with a gentle tap on the device.

Accordingly, the embodiment of FIGS. 9, 10 and 11 provides a new non-invasive method of monitoring heart rate using inertial sensors embedded with gyroscope at the level of the ear (as an embedded tool in an ear-level device such as a hearing aid, a cochlear implant, or a communication device). The sensor is mounted for other significant purposes like estimation of directionality etc. where the measurement of heart rate is a significant outcome of it.

The periodic heart vibration is propagated to the body which the highly sensitive gyroscope captures. This measurement can be used to monitor heart rate. The ear-level inertial sensors provide significant advantage over wristband wearables in terms of stability. Ear-level inertial sensors enable to record heart rate on hearing device users with no extra mounting of other biosensors.

REFERENCE NUMERALS

100—hearing aid instrument
110—signal input
120—microphone
130—audio signal processing unit
140—output transducer
150—surface electrode
160—signal conditioning unit
170—sensor signal processing unit
180—light sensor
190—signal conditioning unit
200—memory unit
210—wireless data interface
220—communication module
230—smart phone
240—inertial sensor
250—signal conditioning unit
300—evaluation unit
310—behind-the-ear part
320—in-the-ear part

The invention claimed is:

1. Hearing aid system comprising an audio signal input, an audio signal processing unit, an output transducer and an ear canal member that is configured to be placed in an ear canal of a human user,
    said audio signal processing unit being operatively connected to said audio signal input and being configured to process electric audio input signals and to generate electric audio output signals,
    said output transducer being operatively connected to said audio signal processing unit and being configured to convert an electric audio output signal generated by the audio signal processing unit into a sound-representing output signal that can be perceived by the user as sound,
    said ear canal member comprising a sensor arrangement comprising
        at least one surface electrode located at a surface of said ear canal member to allow said at least one surface electrode to contact the skin of a user when said ear canal member is operationally mounted on the user, the at least one surface electrode being adapted to pick up a low voltage electric signal from the user's skin, and
        a light sensor located at a surface of said housing to allow emitting light through skin proximate to the light sensor and capturing reflected and/or scattered light when said ear canal member is operationally mounted on the user,
    said hearing aid system further comprising a sensor signal processing unit connected to said surface electrode and said light sensor and being configured to generate one or more sensor signals from each respective output signal of said at least one surface electrode and said light sensor,
    said hearing aid system further comprising or being connected to an evaluation unit that is configured to generate
        an electrocardiogram-representing signal (ECG) from low voltage electric signals picked-up by said at least one surface electrode,
        a plethysmographic-curve-representing signal from an output signal of said light sensor, and
        determine one or more physiological parameter values comprising at least one of a duration of a pre-ejection-period (PEP), a duration of a pulse-transit-time (PTT), and a blood pressure.

2. Hearing aid system according to claim 1, wherein said light sensor is a pulse oximeter.

3. Hearing aid system according to claim 1, further comprising an inertial sensor for sensing movements of the ear canal member when said ear canal member is operationally mounted on the user.

4. Hearing aid system according to claim 3, wherein the inertial sensor is a gyroscope.

5. Hearing aid system according to claim 1, wherein the hearing aid system further comprises a behind the ear part that comprises a further surface electrode located at a surface of said behind the ear part to allow said further electrode to contact the skin of a user when said behind the ear part is operationally mounted on the user, the further surface electrode being adapted to pick up a low voltage electric signal from the user's skin.

6. Hearing aid system according to claim 1, wherein the hearing aid system comprises at least one hearing aid instrument, said hearing aid instrument comprising said audio signal input, said audio signal processing unit, said output transducer and said ear canal member that comprises said sensor arrangement.

7. Hearing aid system according to claim 1, wherein the hearing aid system comprises two hearing aid instruments, each hearing aid instrument comprising at least one surface electrode.

8. Hearing aid system according to claim 1, wherein the hearing aid system comprises at least one hearing aid instrument, said hearing aid instrument comprising an in-the-ear part and a behind-the-ear part, wherein said in-the-ear part comprises said ear canal member comprising said at least one surface electrode and wherein said behind-the-ear part comprises a further surface electrode.

9. Hearing aid system according to claim 1, wherein the hearing aid system comprises at least one hearing aid instrument, said hearing aid instrument comprising a memory unit and a wireless data interface that is operatively connected to said memory unit.

10. Hearing aid system according to claim 9, wherein said hearing aid instrument is configured to wirelessly communicate with said evaluation unit via said wireless data interface.

11. Method for monitoring values of a physiological parameter, said method comprising:
  picking up physiological signals by means of a sensors arranged on or in a hearing instrument, said sensors comprising at least one of a surface electrode, a light sensor and/or an inertial sensor,
  processing said physiological signals and generating one or more sensor signals from each respective output signal of said sensors,
  evaluating said sensor signals to generate at least one of
    an electrocardiogram-representing signal (ECG) from low voltage electric signals picked-up by said at least one surface electrode,
    a plethysmographic-curve-representing signal from an output signal of said light sensor, and/or
    a ballistocardiogram-representing signal (BCG) from an output signal of said inertial sensor, and
  determining values representing a duration of a pre-ejection-period (PEP).

12. Method for monitoring values of a physiological parameter, said method comprising:
  picking up physiological signals by means of a sensors arranged on or in a hearing instrument, said sensors comprising at least one of a surface electrode, a light sensor and/or an inertial sensor,
  processing said physiological signals and generating one or more sensor signals from each respective output signal of said sensors,
  evaluating said sensor signals to generate at least one of
    an electrocardiogram-representing signal (ECG) from low voltage electric signals picked-up by said at least one surface electrode,
    a plethysmographic-curve-representing signal from an output signal of said light sensor, and/or
    a ballistocardiogram-representing signal (BCG) from an output signal of said inertial sensor, and
  determining values representing a duration of a pulse-transit-time (PTT).

13. Method for monitoring values of a physiological parameter, said method comprising:
  picking up physiological signals by means of a sensors arranged on or in a hearing instrument, said sensors comprising at least one of a surface electrode, a light sensor and/or an inertial sensor,
  processing said physiological signals and generating one or more sensor signals from each respective output signal of said sensors,
  evaluating said sensor signals to generate at least one of
    an electrocardiogram-representing signal (ECG) from low voltage electric signals picked-up by said at least one surface electrode,
    a plethysmographic-curve-representing signal from an output signal of said light sensor, and/or
    a ballistocardiogram-representing signal (BCG) from an output signal of said inertial sensor, and
  determining values representing blood pressure.

* * * * *